United States Patent [19]

Bhalla et al.

[11] 4,431,440

[45] Feb. 14, 1984

[54] METHOD TO ALTER OR CONTROL THE DEVELOPMENT AND/OR THE LIFE CYCLE OF VARIOUS PLANT SPECIES

[75] Inventors: Prithvi R. Bhalla, Hightstown; Bryant L. Walworth, Pennington, both of N.J.

[73] Assignee: American Cyanamid Company, Stamford, Conn.

[21] Appl. No.: 333,233

[22] Filed: Dec. 21, 1981

Related U.S. Application Data

[63] Continuation-in-part of Ser. No. 236,471, Feb. 20, 1981, abandoned.

[51] Int. Cl.$^3$ .............................................. A01N 43/54
[52] U.S. Cl. ........................................ 71/92; 544/289
[58] Field of Search ...................................... 71/92, 76

[56] References Cited

U.S. PATENT DOCUMENTS

| | | | |
|---|---|---|---|
| 3,905,800 | 9/1975 | Dominy et al. | 71/76 |
| 4,087,422 | 5/1978 | Bowie et al. | 71/92 |
| 4,147,528 | 4/1979 | McNulty et al. | 71/76 |

FOREIGN PATENT DOCUMENTS 507164  11/1954  Canada .................................... 71/76

OTHER PUBLICATIONS

Reddy et al., "Condensation of o-substituted, etc.;" (1978) CA 91, No. 91587q, (1979).
Patel et al., "Niementowski 4-oxyquinazoline, etc.;" (1968) CA 69, No. 43887n, (1968).

*Primary Examiner*—Glennon H. Hollrah
*Attorney, Agent, or Firm*—H. G. Jackson

[57] ABSTRACT

The invention relates to a method to influence, alter or control the growth, development and/or life cycle of desirable and undesirable plants, comprising: applying to same a biologically effective amount of certain substituted quinazolinones.

The invention also relates to certain novel quinazolinones, useful to influence, alter or control the growth, development and/or life cycle of desirable and undesirable plants.

3 Claims, No Drawings

METHOD TO ALTER OR CONTROL THE DEVELOPMENT AND/OR THE LIFE CYCLE OF VARIOUS PLANT SPECIES

This application is a continuation-in-part of copending application U.S. Ser. No. 236,471, filed Feb. 20, 1981, now abandoned.

SUMMARY OF THE INVENTION

The present invention relates to a method to influence, alter or control the growth, development and/or life cycle of desirable and undesirable monocotyledonous and dicotyledonous plant species, such as broadleaf weeds and grasses and agronomic and horticultural crops, comprising: applying to the foliage and stems of said plants or to the soil in which the seeds and other propagating organs of said plants germinate and grow a biologically effective amount of a compound of formula (I)

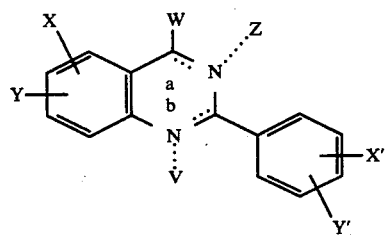

wherein X, X', Y and Y' each are independently selected from the group consisting of hydrogen, alkyl $C_1$-$C_4$, halogen, $CF_3$, $OCH_3$, $OCF_3$, COOR, $SCH_3$, $NO_2$, $NH_2$, OH; R is selected from hydrogen or alkyl $C_1$-$C_3$; the symbols: ······· (a and b) each may independently represent a single or double bond; V is hydrogen or an electron pair and W is selected from oxo, halogen, $OCH_3$ and $N(CH_3)_2$; provided that when a is a single bond, then Z is selected from hydrogen or methyl; and when b is a single bond V is hydrogen; and with the further provisos that when W is oxo and a is a single bond and b is a double bond then the compound has the formula (Ia)

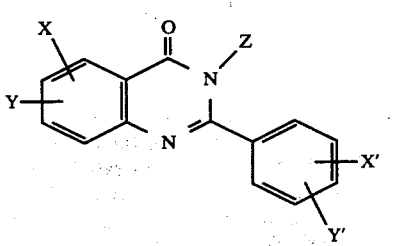

wherein X, X', Y, Y' and Z are defined above; and when W is oxo and both a and b represent single bonds then the compound has the formula (Ib)

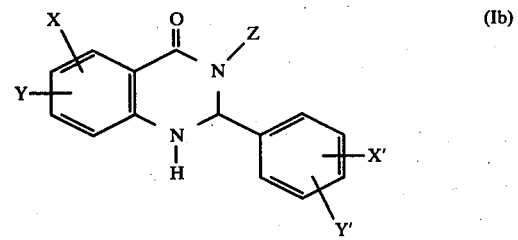

wherein X, X', Y, Y' and Z are as defined above; and when W is selected from halogen, $OCH_3$ and $N(CH_3)_2$, then both a and b represent double bonds, and the compound has the formula (Ic)

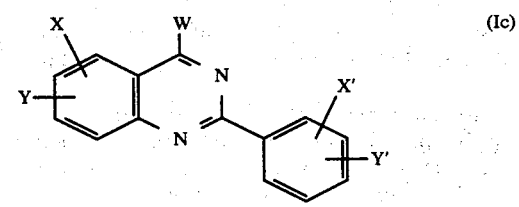

wherein X, X', Y and Y' are hereinabove defined.

In particular, the invention relates to a method for the pre- and postemergence control of undesired mono and dicotyledonous plant species comprising: applying to the foliage and stems of said plants or to the soil in which the seeds and other propagating organs of said plants germinate and grow a herbicidally effective amount of a compound of formula (I).

The invention further relates to a method to beneficially influence, alter or control the growth, development and life cycle of agronomic and horticultural crops, comprising: applying to said crops a compound of formula (I) in amounts sufficient to bring about and/or cause the above referred to beneficial biological changes. In particular, said changes are notable as increased branching with increased number of flowers, earlier bloom and increased pod set, indicative of increased crop yields in legumes, especially in soybeans; while in cereals and especially in rice and barley improved crop yields, increased tillering and earlier maturing are noted among said beneficial changes.

The invention also relates to a group of novel compounds which influence, alter or control the growth development and/or life cycle of desirable and undesirable monocotyledonous and dicotyledonous plant species when applied to same in biologically effective amounts. These compounds may be represented by formula (Ia) structure and defined as follows:

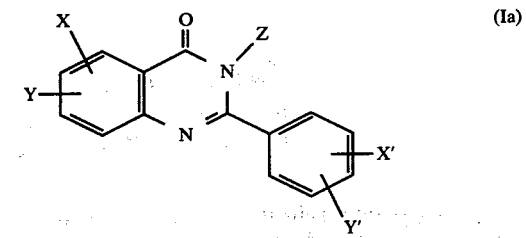

wherein X is hydrogen; Y and X' each are selected independently from hydrogen or chlorine; Y' is selected from alkyl $C_1$–$C_3$, chlorine, $CF_3$, $OCF_3$, $SCH_3$ and $COOCH_3$; and Z is hydrogen.

Among the compounds represented by formula (I), the following are of particular interest:

5-Chloro-2-(4-methylphenyl)-4(3H)-quinazolinone;
6-Chloro-2-(4-methylphenyl)-4(3H)-quinazolinone;
2-Phenyl-4(3H)-quinazolinone;
2-(4-Methylphenyl)-4(3H)-quinazolinone;
2-(4-Chlorophenyl)-4(3H)-quinazolinone;
2-(2,4-Dichlorophenyl)-4(3H)-quinazolinone;
2-(4-Methoxyphenyl)-4(3H)-quinazolinone;
2-(3-Methylphenyl)-4(3H)-quinazolinone;
7-Chloro-2-(3-methylphenyl)-4(3H)-quinazolinone;
6-Chloro-2-(4-chlorophenyl)-4(3H)-quinazolinone;
2-(4-Chlorophenyl)-6-methyl-4(3H)-quinazolinone;
2-(4-Bromophenyl)-6-methyl-4(3H)-quinazolinone;
6-Methyl-2-(4-methylphenyl)-4(3H)-quinazolinone; and
8-Chloro-2-(4-methylphenyl)-4(3H)-quinazolinone.

Advantageously, the compounds of the invention may be prepared by a number of procedures described in the art (W. L. F. Armarego: "Advances in Heterocyclic Chemistry" Vol. 24. Academic Press. N.Y. 1979; and W. L. F. Armarego: "Fused Pyrimidines Part 1-Quinazolines". Willy. N.Y. 1967); and hereinbelow briefly illustrated.

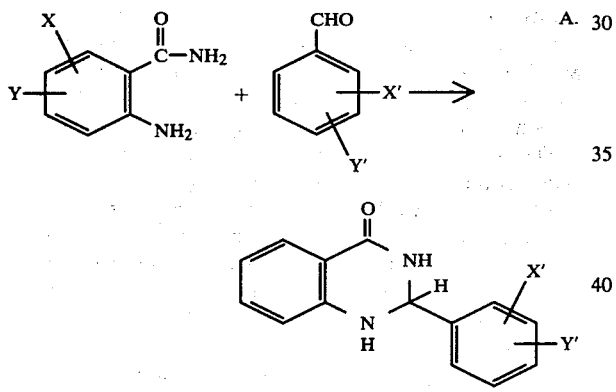

An appropriately substituted benzamide and benzaldehyde are condensed to afford the corresponding 1,2,3,4-tetrahydro-4-oxoquinazoline.

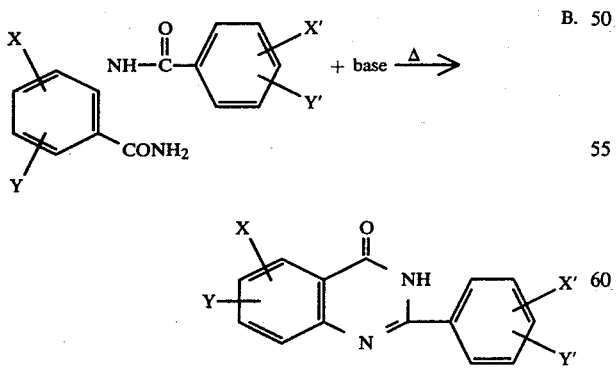

An appropriately substituted benzanilide is ringclosed in the presence of a base at elevated temperatures to afford the corresponding 2-arylquinazolin-4(3H)-ones.

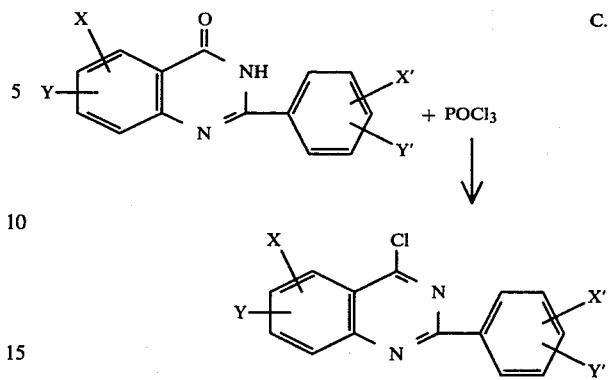

An appropriately substituted 2-arylquinazolin-4-(3H)-one is reacted with phosphorus oxychloride to yield the corresponding 2-aryl-4-chloroquinazoline.

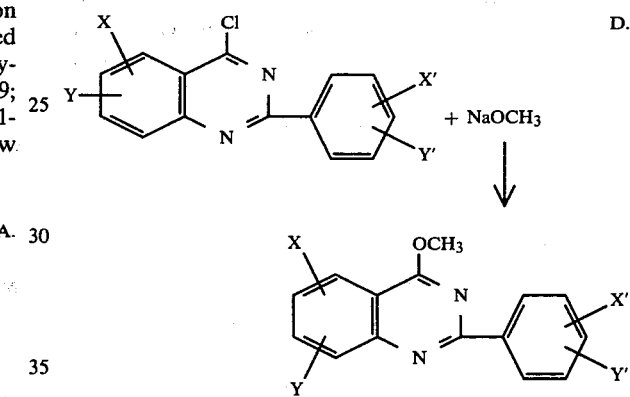

An appropriately substituted 2-aryl-4-chloroquinazoline is reacted with sodium methoxide in the presence of an inert anhydrous solvent to afford the corresponding 4-methoxy analog.

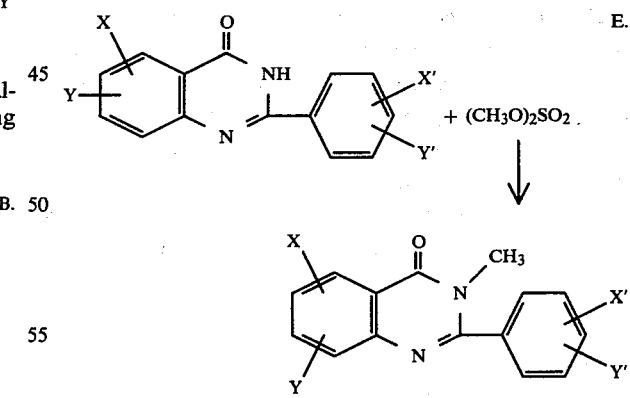

An appropriately substituted 2-aryl-quinazolin-4-one is treated with dimethyl sulfate to yield the corresponding 3-methyl analog. In the above illustrated reaction schemes X, X', Y and Y' are as hereinabove defined.

As stated above, the compounds represented by formula (I) are useful herbicidal agents for the control of undesirable monocotyledonous and dicotyledonous plants. They are highly effective for the preemergence control of said undesirable plants when applied at a rate of from about 2 kg per hectare to about 10 kg per hectare and preferably 5 to 10 kg per hectare to soil containing the seeds, seedlings or propagating organs of broadleaf weeds or grass plants.

The compounds of formula (I) are also effective for the postemergence control of said undesirable plants when applied at the rate of from about 4 kg per hectare to about 10 kg per hectare and preferably 5 to 10 kg per hectare to the foliage of said plants.

The formula (I) compounds and especially the formula (Ia) quinazolinones are surprisingly effective for inducing tillering and increasing the yield of cereal crops such as wheat, barley, rye, oats, corn, and especially rice when applied to said plants in amounts of from about 0.1 kg per hectare to about 1 kg per hectare.

Interestingly, formula (I) compounds, when applied to legumes such as soybeans, beans, peas and lentils in amounts of from about 0.1 kg per hectare to about 1 kg per hectare and preferably 0.5 kg per hectare will improve the axillary branching, will induce increased flowering and increased pod set with concomitant increase in dry pod weight, all of which are suggestive of increased yields.

Advantageously, the compounds of this invention can be formulated as solid or liquid compositions which may be dispersed in a liquid or solid diluent for the application to vegetative matter.

These compounds can be formulated as wettable powders, flowable concentrates, emulsifiable concentrates and granular formulations.

Wettable powders can be prepared by grinding together about 20% to 45% by weight of a finely divided carrier such as kaolin, bentonite, diatomaceous earth, attapulgite, or the like, 45% to 80% by weight of the active compound, 2% to 5% by weight of dispersing agent such as sodium lignosulfonate, and 2% to 5% by weight of a nonionic surfactant such as octylphenoxy polyethoxy ethanol, nonylphenoxy polyethoxy ethanol or the like.

A typical flowable concentrate can be prepared by admixing about 40% by weight of the active ingredient with about 2% by weight of a gelling agent such as bentonite, 3% by weight of a dispersing agent such as sodium lignosulfonate, 1% by weight of polyethylene glycol and 54% by weight of water.

A typical emulsifiable concentrate can be prepared by dissolving about 25% by weight of the active ingredient in about 65% by weight of N-methylpyrrolidone, isophorone, butyl cellosolve, methylacetate or the like and dispersing therein about 10% by weight of a nonionic surfactant such as an alkylphenoxy polyethoxy alcohol. This concentrate is dispersed in water for application as a liquid spray.

When the above compounds are to be used where soil treatments are involved, the compounds may be prepared and applied as granular products. Preparation of the granular product can be achieved by dissolving the active compound in a solvent such as methylene chloride, N-methylpyrrolidone or the like and spraying the thus prepared solution on a granular carrier such as corncob grits, sand, attapulgite, kaolin or the like.

The invention is further illustrated by the examples set forth below.

EXAMPLE 1

Preparation of 2-(4-methylphenyl-4(3H)-quinazolinone

An intimate mixture of p-toluamide (75.2 g; 0.556 mol) and isatoic anhydride (90.8 g; 0.556 mol) is heated at 190° C. for 1.75 hours, while the water formed in the reaction is removed. The mixture is cooled down, ground to a fine powder and extracted with boiling ethanol. The alcoholic extract yields 58.0 g of a yellow powder which is shown to be a mixture of p-toluamide and title product. This yellow powder is recrystallized from ethanol to yield 24.0 g of p-toluamide. Concentration of the mother liquor affords 13 g title product. This material is recrystallized from methanol-methylene chloride and then from acetone to afford 6.4 g of pure product, m.p. 238°–239° C. [R. Pater, J. Het. Chem 8, 699 (1971) gives m.p. of 240° C.].

By the above procedure, but substituting various derivatives of benzamide and isatoic anhydride in the reaction 5-chloro-2-(4-methylphenyl)-4(3H)-quinazolinone, 6-chloro-2-(4-methylphenyl)-4(3H)-quinazolinone, 2-(4-chlorophenyl)-4(3H)-quinazolinone, 6-chloro-2-(4-chlorophenyl)-4(3H)-quinazolinone, 2-(2,4-dichlorophenyl)-4(3H)-quinazolinone and 2-(4-bromophenyl)-6-methyl-4(3H)-quinazolinone can be prepared respectively.

EXAMPLE 2

Preparation of 2'-carbamoyl-p-toluanilide

To a well stirred mixture of anthranilamide (34.05 g; 0.25 mol), methylene chloride (650 ml) and triethylamine (~30 ml) is added p-toluoyl chloride (33 ml; 0.25 mol) dropwise over 25 minutes (a slight exotherm is noted). On completion of the addition, the reaction mixture is stirred for one hour, diluted with water (1000 ml). The mixture is stirred vigorously, filtered, the product washed with water and dried to afford 56.08 g solid, mp 206°–208° C.

EXAMPLE 3

Preparation of 2-(4-methylphenyl)-4(3H)-quinazolinone

A mixture of 2'-carbamoyl-p-toluanilide (66.97 g; 0.263 mol), sodium hydroxide (41.9 g) and water 837 ml) is stirred and heated at reflux for 0.5 hour. The resultant solution is cooled down, made acid with acetic acid. The reaction mixture is filtered, the isolated product is washed and dried to afford 58.16 g off white solid, mp 239°–241° C. Recrystallized from absolute ethanol, the product has a mp of 239°–240.5° C.

EXAMPLE 4

Preparation of Various Substituted Quinazolinones

By the methods of Examples 1, 2 and 3, a number of quinazolinones of the following structure are prepared and are summarized as follows:

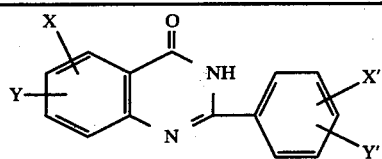

| No | X | Y | X' | Y' | mp °C. |
|----|---|---|----|----|--------|
| 1 | H | H | H | H | 235–238 |
| 2 | H | H | H | p-CH3 | 239–240.5 |
| 3 | H | H | H | o-CH3 | 222–224 |
| 4 | H | H | H | m-CH3 | 211–215 |
| 5 | H | H | H | p-CF3 | 312–314 |
| 6 | H | H | H | p-OCH3 | 245–246.5 |
| 7 | H | H | H | o-COOH | 229–232 |
| 8 | H | H | H | p-OCF3 | 263–267 |
| 9 | H | H | H | m-OCF3 | 223–225 |

-continued

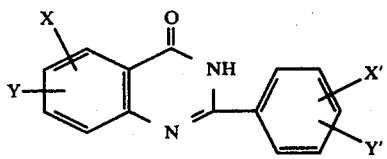

| No | X | Y | X' | Y' | mp °C. |
|----|---|---|----|----|--------|
| 10 | H | H | H | p-C$_2$H$_5$ | 227–229 |
| 11 | H | H | H | p-OH | 300–302 |
| 12 | H | H | H | p-SCH$_3$ | 234–236 |
| 13 | H | H | H | p-t-C$_4$H$_9$ | 224–226 |
| 14 | H | H | H | p-i-C$_3$H$_7$ | 210–210 |
| 15 | H | H | H | o-COOCH$_3$ | 167–170 |
| 16 | H | H | H | p-Br | — |
| 17 | H | H | H | p-NO$_2$ | — |
| 18 | H | H | 2-Cl | 4-Cl | 246–249 |
| 19 | H | H | 2-Cl | 3-Cl | 251–252 |
| 20 | H | 5-Cl | H | p-CH$_3$ | 294–296 |
| 21 | H | 6-Cl | H | p-CH$_3$ | 297–300 |
| 22 | H | H | H | p-Cl | 307–309 |
| 23 | H | 6-Cl | H | H | 293.5–294.5 |
| 24 | H | 6-n-C$_4$H$_9$ | H | p-OCH$_3$ | 214–216 |
| 25 | H | 6-OCH$_3$ | H | H | 257–258.5 |
| 26 | H | H | H | p-NH$_2$ | — |
| 27 | H | 8-OCH$_3$ | H | p-OCH$_3$ | 231–233 |
| 28 | H | H | 2-OH | 3-CH$_3$ | 278–280 |
| 29 | H | H | 2-OH | 4-Cl | 345–347 |

EXAMPLE 5

Preparation of Substituted Tetrahydro-4-Oxo-Quinazolines

Utilizing the art disclosed methods of the reaction sequence of "A", a number of compounds of the corresponding structure are prepared. These are listed as follows:

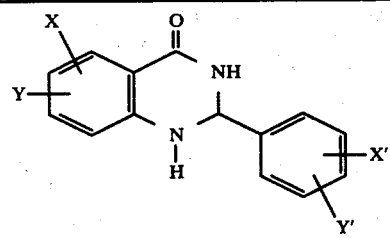

| No | X | Y | X' | Y' |
|----|---|---|----|----|
| 1 | H | H | H | m-Cl |
| 2 | H | H | H | p-Cl |
| 3 | H | H | H | m-CH$_3$ |
| 4 | H | H | 2-Cl | 6-Cl |
| 5 | H | H | 2-CH$_3$ | 5-CH$_3$ |
| 6 | H | H | H | 4-i-C$_3$H$_7$ |
| 7 | H | H | H | p-CH$_3$ |

EXAMPLE 6

Preparation of Substituted Quinazolines

Utilizing the art disclosed methods of the reaction sequences of "C" and "D", a number of compounds are prepared as listed below.

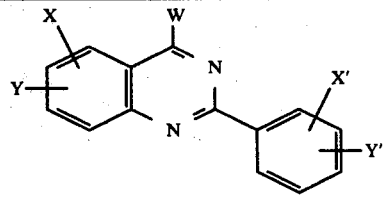

| No | X | Y | X' | Y' | W | mp °C. |
|----|---|---|----|----|---|--------|
| 1 | H | H | H | H | Cl | 124–125 |
| 2 | H | H | H | p-OCH$_3$ | Cl | — |
| 3 | H | H | H | p-NO$_2$ | Cl | — |
| 4 | H | H | H | p-Br | Cl | — |
| 5 | H | H | H | p-Cl | Cl | 166–167 |
| 6 | H | H | H | p-Cl | OCH$_3$ | 125–126 |
| 7 | H | H | H | p-CH$_3$ | Cl | 113–115 |
| 8 | H | H | H | p-CH$_3$ | OCH$_3$ | 75–79 |

EXAMPLE 7

Preparation of 3-Methylquinazolinones

The appropriate, substituted quinazolin-4-ones are reacted with dimethyl sulfate under art disclosed conditions to yield the corresponding 3-methyl analogs shown below:

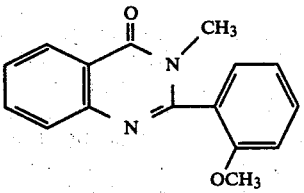

mp 188–190° C.

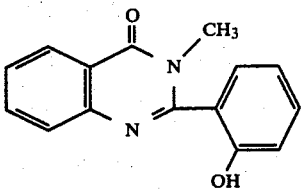

mp 223–225° C.

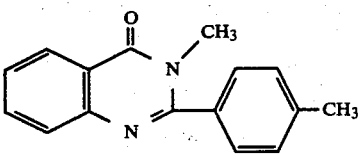

mp 136–140° C.

EXAMPLE 8

Evaluation of the Preemergence Herbicidal Activity of the Compounds of the Invention The preemergence herbicidal activity of the compounds of the present invention is exemplified by the following tests in which the seeds or propagating organs of a variety of monocotyledonous and dicotyledonous plants are mixed with potting soil and planted on top of approximately 2.5 cm soil in separate cups. After planting, the cups are sprayed with the selected aqueous acetone solution containing test compound in sufficient quantity to provide the equivalent to the kg/ha amount(s) shown in Table I below per cup. The treated cups are then placed on greenhouse benches, watered and cared for in accordance with conventional greenhouse procedures. Three to five weeks after treatment, the tests are terminated and each cup is examined and rated according to the rating system provided below. The data obtained are reported in Table I below.

| Rating System | Difference in Growth from the Check |
|---|---|
| o - No effect | 0 |
| 1 - Trace Effect | 1-5 |
| 2 - Slight effect | 6-15 |
| 3 - Moderate effect | 16-29 |
| 4 - Injury | 30-44 |
| 5 - Definite injury | 45-64 |
| 6 - Herbicidal effect | 65-79 |
| 7 - Good herbicidal effect | 80-90 |
| 8 - Approaching complete kill | 91-99 |
| 9 - Complete Kill | 100 |
| "P" - "PGR" effect | — |

Test species are observed for plant growth regulant effects of the chemicals during all herbicide evaluations. If such effects occur, a rating of "P" is entered for the species affected along with a PGR notation (from Notation Table).

PLANT ABBREVIATIONS

NS = Purple nutsedge (*Cyperus rotundus*)
SE = Sesbania (*Sesbania exaltata*)
MU = Mustart (*Brassica kaber*)
PI = Pigweed (*Amaranthus retroflexus*)
RW = Ragweed (*Ambrosia artemisiifolia*)
MG = Morningglory (*Ipomoea purpurea*)
PS = Prickly sida (*Sida spinosa*, L)
VL = Velvetleaf (*Abutilon theophrasti*)
BA = Barnyardgrass (*Echinochloa crusgalli*)
CR = Crabgrass (*Digitaria sanguinalis*)
FO = Green Foxtail (*Setaria viridis*)
WO = Wild Oats (*Avena fatua*)

TABLE I

Evaluation of the preemergence herbicidal activity of the compounds of the invention.

| Compound | Rate kg/ha | NS | SE | MU | PI | RW | MG | PS | VL | BA | CR | FO | WO |
|---|---|---|---|---|---|---|---|---|---|---|---|---|---|
| 2-(4-methylphenyl)-4(3H)-quinazolinone | 5.0 | 9 | 7 | 9 | 9 | 8 | 8 | 8 | 8 | 6 | 7 | 7 | 8 |
| 2-(2,4-dichlorophenyl)-4(3H)-quinazolinone | 8.0 | 9 | — | 8 | — | — | 5 | 2 | — | — | — | — | 2 |
| 2-(p-chlorophenyl)-4(3H)-quinazolinone | 8.0 | 9 | — | 8 | — | 7 | 7 | 6 | 5 | — | — | — | 7 |

EXAMPLE 9

Evaluation of the Postemergence Herbicidal Activity of the Compounds of the Invention The postemergence herbicidal activity of the compounds of the invention is demonstrated by the following tests, wherein a variety of monocotyledonous and dicotyledonous plants are treated with test compounds dissolved (or dispersed) in aqueous acetone mixtures. In the tests, seedling plants are grown in separate cups for about two weeks. The test compounds are dissolved (or dispersed) in 50/50 acetone/water mixtures containing 0.5% TWEEN® 20, a polyoxyethylene sorbitan monolaurate surfactant of Atlas Chemical Industries, in sufficient quantity to provide the equivalent to the kg/ha amount(s) shown in Table II when applied to the plants through a spray nozzle operating at 2.81 kg/cm² pressure for a predetermined time. After spraying, the plants are placed on greenhouse benches and are cared for in the usual manner, commensurate with conventional greenhouse practices. Five weeks after treatment, the seedling plants are examined and rated according to the rating system set forth in Example 8. The data obtained are reported in Table II below.

TABLE II

Evaluation of the postemergence herbicidal activity of the compounds of the invention.

| Compound | Rate kg/ha | SE | MU | PI | RW | MG | PS | VL | BA | CR | FO | WO |
|---|---|---|---|---|---|---|---|---|---|---|---|---|
| 2-(4-methylphenyl)-4(3H)-quinazolinone | 5.0 | 3 | 9 | 8 | 0 | 7 | 3 | 7 | 6 | 0 | 7 | 8 |

EXAMPLE 10

Evaluation of the Morphological Effects of the Compounds of the Invention on Barley, Corn and Soybeans In the following tests, the appropriate compound(s) are dissolved or dispersed in acetone/water (50/50) mixtures at the final concentration corresponding to the kg/ha rates indicated in the tables below. The solutions also contain 0.1% to 0.25% V/V colloidal BIOFILM® (a product of Colloidal Products Corp.) which is a mixture of alkyl aryl polyethoxyethanol, free and combined fatty acids, glycol ethers, dialkylbenzene carboxylate and 2-propanol.

The plant species used in these tests are barley (*Hordeum vulgare*, var. Mexico), corn (*Zea mays*, var. Dekalb) and soybeans (*Glycine max*, var. Adelphia).

The solution or dispersion of the compound under test is sprayed at a rate of 40 ml per pot applied to the foliage.

In the postemergence tests, the barley seedlings are at the two leaf stage, and are on the average 13 cm tall (22 plants per pot; pot size 8.9 cm × 6.3 cm × 6.3 cm); the corn seedlings are at the four leaf stage, and are on the average 9 cm tall (one plant per pot; pot size as above); and the soybean seedlings are at the second trifoliate stage, and are on the average 16 cm tall (one plant per pot; pot size as above).

The pots are watered, treated and placed on benches in a random arrangement in the greenhouse. Normal watering and fertilizing practices are followed (pesticides are applied to the plants as needed). Minimum day and night temperatures of 18.3° C. are maintained during cooler period of the year. Normal daily fluctuations occur during the summer season.

Plants are sprayed to provide the kg/ha rates indicated in the tables below. Each treatment is replicated six times.

Data Recording

Periodic observations are made after treatment and morphological changes are noted. From these observations as compared to the untreated controls, the effect(s) of the instant compounds on the various plant species can be determined.

The data thus obtained are averaged and summarized in Tables IIIa to IIIc inclusive.

TABLE IIIa

Evaluation of the growth regulating effects of the compounds of the invention on barley.

| Compound | Rate:kg/ha | Results |
|---|---|---|
| 2-(4-methylphenyl)-4(3H)-quinazolinone | 1.0 | Slight increase in tillering; 0–10% increase in height and fresh weight. |
| | 0.5 | Slight increase in tillering 0–10% increase in height and fresh weight. |
| | 0.1 | 0–10% increase in height and fresh weight. |

TABLE IIIb

Evaluation of the growth regulating effects of the compounds on soybeans.

| Compound | Rate: kg/ha | Results |
|---|---|---|
| 2-(4-methylphenyl)-4(3H)-quinazolinone | 1.0 | Moderate increase in branching and in earlier or more flower buds; 0–10% increase in height, 21–30% increase in fresh weight, 11–20% increase in dry weight. |
| | 0.5 | Moderate increase in branching and in earlier or more flower buds; 0–10% increase in height, 21–30% increase in fresh weight, 11–20% increase in dry weight. |
| | 0.1 | Moderate increase in branching, slight increase in earlier or more flower buds; 0–10% increase in height, 11–20% increase in fresh weight, 0–10% increase in dry weight. |

TABLE IIIc

Evaluation on the growth regulating effects of the compounds on corn.

| Compound | Rate: kg/ha | Results |
|---|---|---|
| 2-(4-methylphenyl)-4(3H)-quinazolinone | 1.0 | 0–10% increase in height and fresh weight. |
| | 0.5 | 0–10% increase in height and fresh weight |
| | 0.1 | 0–10% increase in height, 0–19% decrease in fresh weight. |

EXAMPLE 11

Evaluation of the Effect of a Compound of the Invention on the Growth and Yield of Soybeans By the method of Example 10, the effect of a compound of the invention is evaluated on soybeans (*Glycine max*, var. Adelphia). Each test is replicated six times. There is one plant per pot, and the plants are treated at the second trifoliate stage. The plants are harvested two months post treatment; the data obtained are averaged and summarized in Table IV below.

TABLE IV

The effect of a compound of the invention on the growth and yield of soybeans.

| Compound | Rate: kg/ha | No. of Pods | Fresh Pod Wt. in g | Dry Pod Wt. in g |
|---|---|---|---|---|
| Control | — | 61.4 | 62.5 | 16.1 |
| 2-(4-methylphenyl)- | 0.5 | 71.8 | 74.1 | 19.7 |
| 4(3H)-quinazolinone | 0.1 | 60.2 | 62.1 | 15.9 |

EXAMPLE 12

Evaluation of the Effect of Compounds of the Invention on Rice

Paddy rice (*oryza sativa* var. IR-36) is planted three plants per hill 25×25 cm apart in 3m² plots in a random block design.

Spray solutions or dispersions of the compound(s) under test are prepared by the method of Example 10 at the final concentrations corresponding to the kg/ha rates indicated in Table V below. Each test is replicated three times.

The rice seedlings are treated at maximum tillering but before pauicle development (i.e. before the stems or culms begin to elongate) and at the time of harvest, the yields per plot are determined, the data are averaged and the percent change ($\pm$) from the untreated controls determined. The thus obtained data are presented in Table V below wherein it can be seen that the compound 2-(4-methylphenyl)-4(3$\underline{H}$)-quinazolinone applied to paddy rice at maximum tillering at 0.5 to 2.0 kg/ha rate increases the product yields from about 6 to about 12% by weight.

TABLE V

Evaluation of the effect of the compounds of the invention on rice

| Compound | Rate kg/ha | Average yield g/plot | Average yield kg/ha | % change from control | kg/ha gain over control |
|---|---|---|---|---|---|
| Control | — | 1417 | 4723.33 | — | — |
| 2-(4-methyl- | 0.5 | 1500 | 5000.00 | +5.86 | 276.67 |
| phenyl)-4(3H) | 1.0 | 1582 | 5273.33 | +11.64 | 550.00 |
| quinazolinone | 2.0 | 1533 | 5110.00 | +8.19 | 386.67 |

EXAMPLE 13

Evaluation of the Effect of a Compound of the Invention on the Early Branching of Soybeans By the method of Example 11, the effect of a compound on the early branching is evaluated on soybeans (*Glycine max*). Each test is replicated five times, and the compounds are applied at a rate of 0.125, 0.25 and 0.5 kg/ha. Two to three weeks after treatment the plants are examined and rated as to changes in branching versus the controls. The data obtained are averaged and summarized in Table VI below.

TABLE VI

Evaluation of the effect of compounds of the invention on the early branching of soybeans

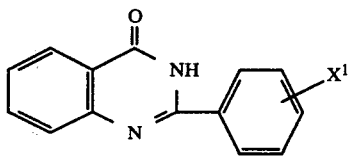

| No | X' | % increase in branching at the kg/ha rate of | | |
|----|------|-------|-------|-------|
|    |      | 0.125 | 0.250 | 0.500 |
| 1  | H    | 0     | 4–6   | 0     |
| 2  | 4-OCH₃ | 0   | 0     | 8–10  |
| 3  | 2-COOH | 0   | 1–3   | 1–4   |
| 4  | 4-CH₃ | 4–6  | 10–11 | 11    |
| 5  | 4-Cl | 0     | 4–6   | 4–6   |

TABLE VI-continued

Evaluation of the effect of compounds of the invention on the early branching of soybeans

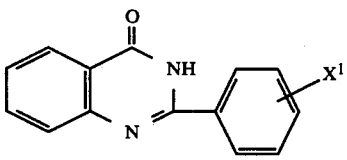

| No | X' | % increase in branching at the kg/ha rate of | | |
|----|------|-------|-------|-------|
|    |      | 0.125 | 0.250 | 0.500 |
| 6  | 2,3-(Cl)₂ | 4–6 | 2–4 | 3–5 |
| 7  | 2-COOCH₃ | 3–5 | 3–5 | 8–10 |
| 8  | 4-C(CH₃)₃ | 5–7 | 3–5 | 0 |
| 9  | 4-OCF₃ | 3–5 | 4–6 | 0 |
| 10 | 4-C₂H₅ | 1–3 | 0 | 0 |
| 11* | 4-CH₃ | 0 | 4–6 | 0 |

* = tetrahydro analog of compound No 4 in the tabulation

We claim:

1. A method to increase the grain yield of cereal crops comprising: applying to the foliage of said plants or to the soil in which said plants or seeds germinate and propagate, an effective amount of a compound 2-(4-methylphenyl)-4(3H) quinazolinone.

2. A method according to claim 1, wherein said cereal crop is rice.

3. The method according to claim 1 wherein the compound is applied at from 0.1 to about 1 kg per hectare.

* * * * *